(12) United States Patent
Yeh et al.

(10) Patent No.: US 6,528,654 B2
(45) Date of Patent: Mar. 4, 2003

(54) SYNTHESIS OF HISTAMINE DIHYDROCHLORIDE

(75) Inventors: Wen-Lung Yeh, Ontario (CA); Casimir Antczak, Ontario (CA); Jeffry David McGolrick, Ontario (CA); Michael Joseph Roth, Ontario (CA); Mark Wrona, Ontario (CA)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/974,469

(22) Filed: Oct. 9, 2001

(65) Prior Publication Data

US 2002/0035268 A1 Mar. 21, 2002

Related U.S. Application Data

(63) Continuation of application No. 09/467,652, filed on Dec. 20, 1999, now Pat. No. 6,403,806.
(60) Provisional application No. 60/113,933, filed on Dec. 23, 1998.

(51) Int. Cl.$^7$ ............................................. C07D 233/64
(52) U.S. Cl. .................................................... 548/335.5
(58) Field of Search ....................................... 548/335.5

(56) References Cited

U.S. PATENT DOCUMENTS

| | | |
|---|---|---|
| 3,717,655 A | 2/1973 | Godefroi et al. |
| 4,772,721 A | 9/1988 | Voelter |
| 5,190,589 A | 3/1993 | Eriks et al. |
| 5,728,378 A | 3/1998 | Hellstrand et al. |

FOREIGN PATENT DOCUMENTS

| | | |
|---|---|---|
| DE | 56793 | 11/1966 |
| GB | 430108 | 6/1935 |
| GB | 1008594 | 10/1965 |
| JP | 5-255204 | 10/1993 |
| SU | 166355 | 11/1964 |

OTHER PUBLICATIONS

Ferrigni, N.R. et al. (1982) Cactus alkaloids. XLVII, Nα, Nα–Dimethylhistamine, A hypotensive component of echinocereus triglochi–diatus. Jour. of Ethnopharmacology. 5:359–364.

Hashimoto. M. et al. (1986) Chemistry Letters. The Chem. Soc. of Japan. 893–896.

Koessler, K.K. et al. (1918) Studies on proteinogenous amines. I. The synthesis of β–Imidazolylethyamine (histamine). 1716–1726.

Pyman, F.L. (1911) LXXIV—A new synthesis of 4(or5–)–β–aminoethyl–glyoxaline, one of the active principles of ergot. Jour. Amer. Chem. Soc. 668–682.

Takano et al. (1977) Efficient synthesis of tryptamine. Heterocycles. 6:1167–1171.

Witte, E.C. (1989) Chemical synthesis of picumast dihydrochloride. Drug Res. 39(II):1309.

Levy–Bruhl et al., "Production of Histaminic Substances by Mucous Bacilli in Synthetic Environment Containing Urea as the only Nitrogenated Food", (1938) Annals of the Pasteur Institute pp. 828–829.

Vitali et al., "Imidazole $H_2$ Agonists—Synthesis and Activity of 2–(2–amino–4imidazolyl)ethylamine (2–aminohistamine) dihydrochloride", III Farmaco Scientific Edition vol. 39—Section 1, 1983.

*Primary Examiner*—Taofiq Solola
(74) *Attorney, Agent, or Firm*—Knobbe, Martens, Olsen & Bear, LLP

(57) ABSTRACT

The invention disclosed herein relates to the preparation of pharmaceutical grades of histamine dihydrochloride using a two step non-enzymatic synthetic method. The invention disclosed herein describes the synthesis of histamine dihydrochloride by the non-enzymatic decarboxylation of histidine and the step-wise conversion of the decarboxylated product to the dihydrochloride salt form. The invention disclosed herein considers a final product of histamine dihydrochloride containing less than each of the following: 0.8% L-histidine HCl monohydrate, 0.1% individual chromatographic impurities, and 2% total impurities, to be acceptable for pharmaceutical use.

8 Claims, 2 Drawing Sheets

SYNTHESIS OF HISTAMINE DIHYDROCHLORIDE

RELATED APPLICATIONS

This application is a continuation of U.S. patent application Ser. No. 09/467,652, filed Dec. 20, 1999, now U.S. Pat. No. 6,403,806 which claims priority to U.S. provisional patent application No. 60/113,933, filed Dec. 23, 1998 both of which are hereby incorporated by reference in their entirety.

BACKGROUND OF THE INVENTION

Histamine is a compound possessing significant biological activity mediated by pharmacological receptors. Histamine has long been contemplated as a molecule having primarily negative biological effects. Recently, however, new uses for histamine as a powerful pharmaceutical agent have come to light. For example, histamine has been used in conjunction with interferon-alpha to activate NK cells (Natural Killer cells) in the presence of monocytes. See U.S. Pat. No. 5,728,378. To take full advantage of the therapeutic properties of histamine, it is necessary to obtain large quantities of the compound in a pharmaceutical grade.

Histamine occurs widely in nature as a result of putrefactive processes and a derivative, histamine dihydrochloride, is sold commercially for use as a standard in assays and as a component in certain allergy diagnostic kits. The source of this histamine is often a natural one and as such contains a variety of contaminants that render it unsuitable for pharmaceutical use. There are also synthetic protocols for the synthesis of histamine dihydrochloride known in the art.

Histamine dihydrochloride can be conveniently synthesized by exploiting the decarboxylation of histidine. Using this synthesis pathway, histidine is decarboxylated and subsequently treated to form the dihydrochloride salt form of the molecule. For example, Hashimoto et al., discussed the preparation of histamine using cyclohexenone as a catalyst for the decarboxylation of histidine. (Hashimoto, M., et al., Chemistry Letters, 893–896 (1986)). The Hashimoto, et al., paper reported the isolation of histamine dihydrochloride at a 95% yield, using 2-cyclohexen-1-one as the catalyst, from the reaction involving histidine and 1% v/v of 2-cyclohexen-1-one in 10 parts of refluxing cyclohexanol (26 hours). The Hashimoto method also teaches the use of toluene and HCl gas bubbled through the resulting decarboxylated solution to precipitate out and harvest the final histamine dihydrochloride product.

Attempts to reproduce the Hashimoto procedure to generate pharmaceutically pure amounts of histamine failed. Additional amounts of the catalyst were required to make the procedure operative and a substantial number of impurities were present in the final product. Moreover, those impurities were difficult to remove. In view of these results, it was found that the Hashimoto procedure is an unsuitable method for generating large quantities of pharmaceutically acceptable histamine.

The use of acetophenone as a catalyst for the decarboxylation of histamine has also been reported. We recreated the method described in the Japanese patent to Akimasa, et al., patent, Japanese Patent No. 05,255,204 (1983), and used 0.26 equivalents of acetophenone and 10 parts of diethylene glycol as the solvent for the decarboxylation reaction. Although the Akimasa et al. method was far more efficient in converting histidine to histamine, it failed to consistently yield a pharmaceutical grade product. Like the final product using the Hashimoto method, impurities were observed in the final product made using the Akimasa method during the HPLC analysis.

Although the conditions with acetophenone and diethylene glycol looked promising, there existed a problem related to the work-up. Both histamine free base and the dihydrochloride salt are readily soluble in water, therefore, it was difficult to utilize any extraction technique to separate the product from the diethylene glycol solvent, which was usually removed by a water extraction. Furthermore, the histamine dihydrochloride was also readily soluble in diethylene glycol, thus the direct isolation by filtration was also impossible.

The reaction conditions of Takano et al., involving pentan-3-one were also recreated. (Heterocycles, 6:1167 (1977)). The results from these experiments showed no improvement over the acetophenone conditions described above.

A consistent source of pharmaceutical grade histamine is required, especially in view of the new-found pharmaceutical applications for histamine. The standard methods used by the art wherein histamine is purified from natural sources, fail to yield histamine of a sufficiently high grade for pharmaceutical uses. Moreover, the synthetic methods practiced in the art also fail to yield histamine of a sufficiently high grade. Accordingly, there is a need in the art for an improved method by which to produce pharmaceutical grade histamine dihydrochloride.

SUMMARY OF THE INVENTION

The invention disclosed herein relates to the preparation of pharmaceutical grades of histamine dihydrochloride using a two step non-enzymatic synthetic method. One embodiment of the invention is a method for the synthesis of histamine dihydrochloride comprising: decarboxylating a L-histidine containing solution, whereby a histamine containing solution is formed in the absence of a decarboxylating enzyme; forming a histamine monohydrochloride containing solution from the histamine containing solution; and forming a histamine dihydrochloride containing solution from the histamine monohydrochloride containing solution.

One aspect of this embodiment further comprises triturating the histamine containing solution, for example, the histamine containing solution can be triturated with a methylene chloride solution. In another aspect of this embodiment, the histamine monohydrochloride containing solution is formed by addition of an effective amount of hydrochloric acid in an isopropanol solution. For example, the effective amount of hydrochloric acid is about 0.1 to 0.9 molar equivalents of hydrochloric acid to histamine free base. In another example, the effective amount of hydrochloric acid is about 0.6 molar equivalents of hydrochloric acid to histamine free base. Still another aspect of this embodiment further comprises the step of isolating a pharmaceutical grade of histamine dihydrochloride from the histamine dihydrochloride containing solution.

Another embodiment of the invention disclosed herein is a method for synthesizing a pharmaceutical grade of histamine dihydrochloride comprising: decarboxylating a L-histidine containing solution, whereby a histamine containing solution is formed in the absence of a decarboxylating enzyme; forming a histamine monohydrochloride containing solution from the histamine containing solution; forming a histamine dihydrochloride containing solution from the histamine monohydrochloride containing solution and isolating the histamine dihydrochloride from the histamine dihydrochloride containing solution.

In one aspect of this embodiment, the histamine dihydrochloride contains equal to or less than each of the following: 0.8% L-histidine HCl monohydrate, 0.1% individual chromatographic impurities, and 2% total impurities.

DETAILED DESCRIPTION OF THE INVENTION

The invention disclosed herein relates to the preparation of pharmaceutical grades of histamine dihydrochloride using a two step non-enzymatic synthetic method. The invention disclosed herein describes the synthesis of histamine dihydrochloride by the non-enzymatic decarboxylation of histidine and the step-wise conversion of the decarboxylated product to the dihydrochloride salt form. The invention disclosed herein considers a final product of histamine dihydrochloride containing less than each of the following: 0.8% L-histidine HCl monohydrate, 0.1% chromatographic impurities (defined below), and 2% total impurities, to be acceptable for pharmaceutical use.

Figure 1:
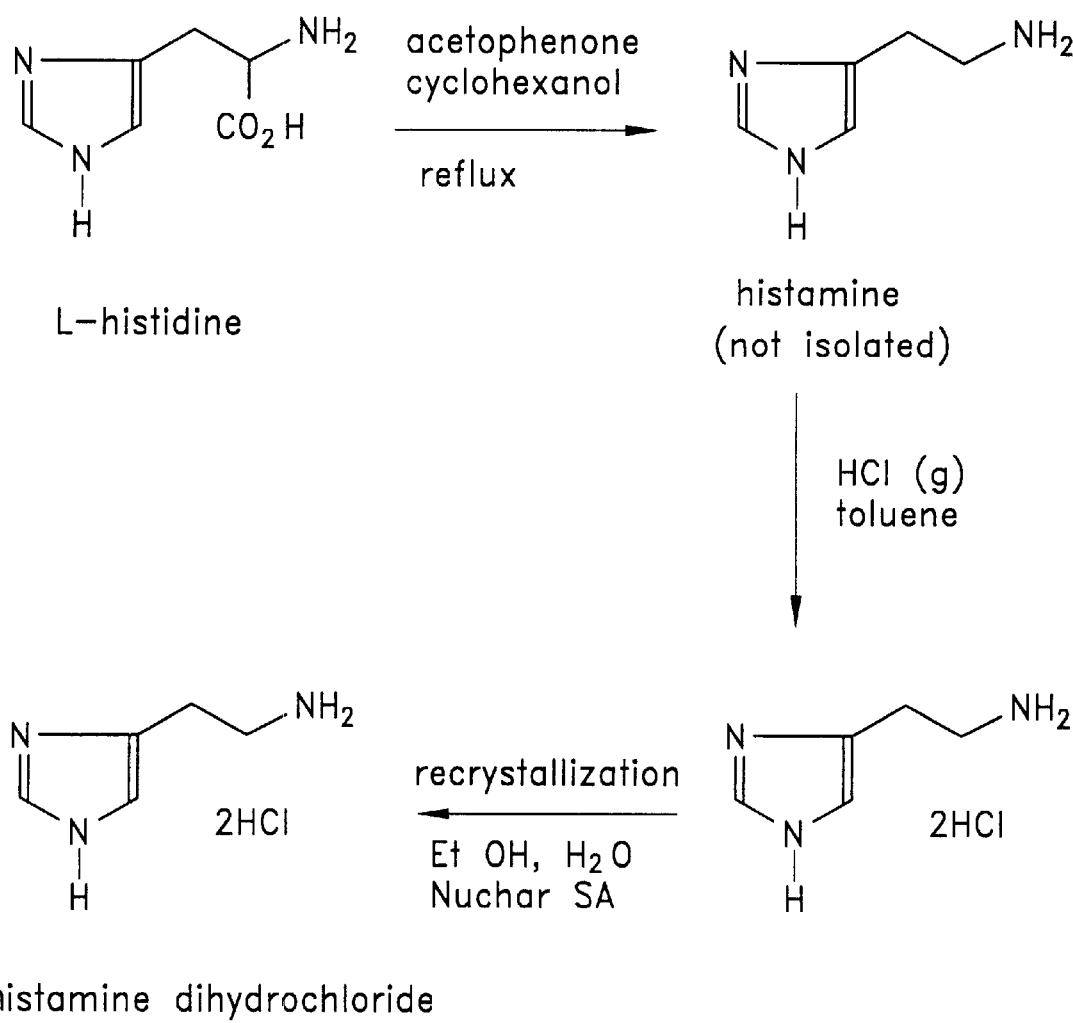
FIG. 1 shows a reaction method taught in the art.
Figure 2:
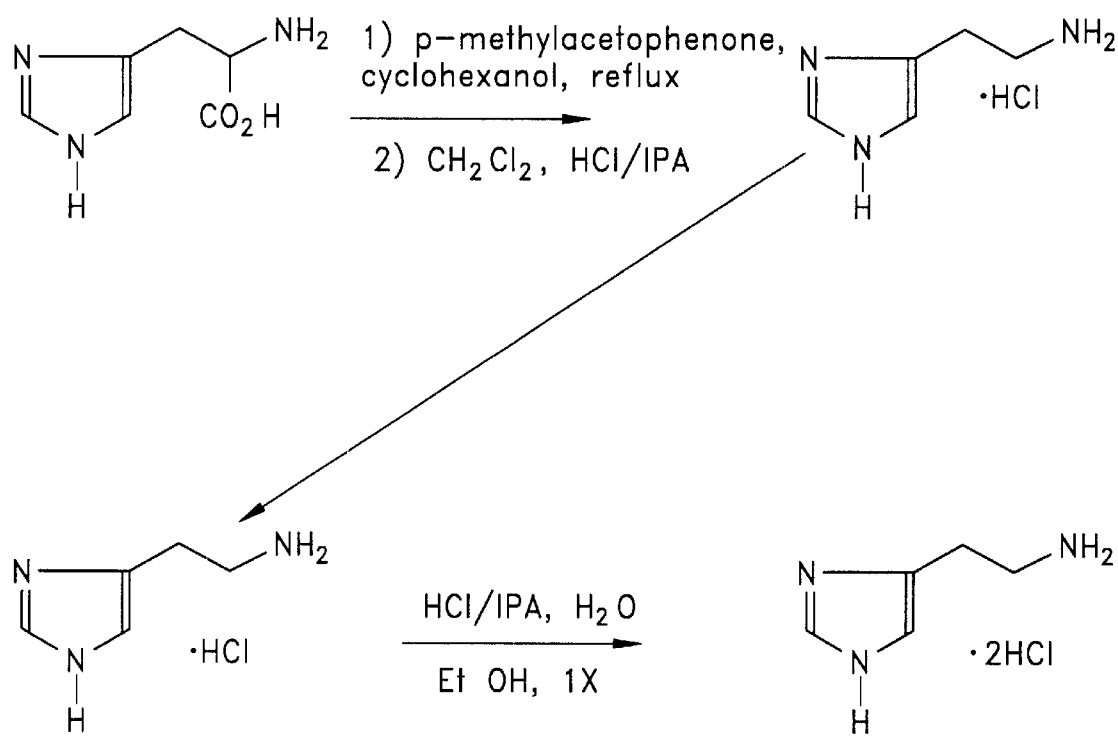
FIG. 2 shows the method of the invention disclosed herein discussed in Examples 5 and 6.

Synthetic methods of synthesizing histamine dihydrochloride known in the art fail to yield product of a sufficient purity to be used as a pharmaceutical compound. FIG. 1 shows a decarboxylation method taught in the art. The method steps of the invention disclosed herein are shown in FIG. 2.

Prior art methods were used to generate histamine dihydrochloride from L-histidine starting material in an attempt to generate pharmaceutical grades of synthetic histamine dihydrochloride. The starting material was reacted with the prior art catalyst α-tetralone and cyclohexane. After completion of the reaction, the sample was cooled and hydrochloric acid was bubbled into the solution to convert the histamine free base into the dihydrochloride salt form. The precipitate that formed was filtered, washed, and dried. The final product produced by the prior art method was found to contain an unacceptably high number of contaminants.

The crude material produced using the prior art method had a purity of 92–94% with one major impurity at 3–5% and five to eight other impurities at >0.1%. Additional purification steps or recrystalizations were performed and were substantially effective at removing most of these contaminants. Nevertheless, two unidentified impurities remained at levels above 0.1%. These impurities eluted after the histamine dihydrochloride product and were referred to as chromatographic impurities or contaminants. Thus, product made by this method was unacceptable for pharmaceutical use.

In view of these results, a new procedure was designed to synthesize histamine dihydrochloride of the desired purity. This new procedure involved the decarboxylation of L-histidine (α-amino-4(or 5)-imidazolepropionic acid ($C_6H_9N_3O_2$) to yield histamine. Following decarboxylation, the solution containing the histamine free base was triturated with methylene chloride to precipitate the product. The product was then filtered and washed. The filtered product was subsequently treated with hydrochloric acid in isopropanol to precipitate a crude histamine monohydrochloride salt. This product was filtered and isolated. The crude salt can be subsequently purified by recrystalization techniques or it can proceed to the final modification step of the present method. Next, the monohydrochloride salt was treated again with a hydrochloric acid/isopropanol solution to generate the histamine dihydrochloride form of the molecule. The final form of the product was then decolorized and washed. These steps, known as recrystalization, can be repeatedly extensively to yield histamine dihydrochloride of pharmaceutical purity. All steps were performed under a nitrogen gas atmosphere. The purity of the final product was analyzed through a number of analytical methods including HPLC analysis.

The invention disclosed herein contemplates the use of a number of catalysts or radical initiators to facilitate the decarboxylation reaction. An appropriate catalyst is one that will efficiently catalyze the decarboxylation of histidine when that precursor compound is in a neutral solvent and heated for a number of hours to yield an acceptably pure final product. Electron-enriched ketones are preferred as they tend to reduce the number of impurities present in the final product. For example, a group of suitable catalysts comprises: benzoyl peroxide, 2,2'-azobisisobutyronitrile (AIBN), 2-cyclohexen-1-one, acetophenone, 4'-bromoacetophenone, benzophenone, p-nitroacetophenone, p-methylacetophenone, p-methoxyacetophenone, p-methylacetophenone/1-methyl-4-piperidone, and p-methylacetophenone/AcOH.

The decarboxylation reaction conditions promote the decarboxylation of the starting materials while minimizing the formation of unwanted contaminants. The reaction conditions include conducting several method steps in the presence of an inert gas, for example, nitrogen. The reaction conditions further include conducting the decarboxylation step at a range of temperatures between about 145 to 170° C. Preferably, the reaction is carried out at a range of temperatures from about 150 to 165° C., or at a range of temperatures from about 160 to 165° C.

A number of solvents are contemplated for use in the invention disclosed herein. The solvents in which certain steps of the reaction are conducted may effect the reaction time which is required to catalyze the decarboxylation of histidine. Solvents useable in the invention disclosed herein include: cyclohexanol, n-methlpyrrolidinone (NMP), di(ethyleneglycol), di(ethyleneglycol)methyl ether, 2-methyloxyethlether, 1-butanol, methoxyethanol, cyclohexanol/NMP (in a 3:1 ratio), dimethylformamide, and tetramethylenesulfone.

Another parameter of the reaction disclosed herein is the method of creating the salt form of histamine by treating the reaction mixture with hydrogen chloride. The impurity profile of the final product was found to be effected by the molar equivalency of acid added during the precipitation of the monohydrochloride crude salt. It is possible to control the extent of impurity formation by preparing a solution of hydrogen chloride of a known concentration in isopropanol and treating the reaction mixture therewith.

A range of molar equivalents of hydrogen chloride (HCl) in isopropanol (ISA) may be used to practice the method of the invention disclosed herein. A range of about 0.01 to 2 molar equivalents may be used to create the salt form of histamine. Alternatively, a range of about 0.05 to 1.4 molar equivalents may be used. In another alternative, a range of about 0.1 to 0.9 molar equivalents may be used. In yet another alternative, about 0.5 molar equivalents may be used. The ratio selected to practice the invention disclosed herein should result in the ultimate generation of a final product with an acceptable level of impurities so that the final product may be used as a pharmaceutical composition.

The concentration of the acidic solution used to create the salt form was not critical. For example, the concentration of HCl in ISA may range from about 6 to 9 N. However, the number of moles of acid introduced is crucial to isolating a pharmaceutically acceptable grade of the final product. The addition of too much acid causes impurities to precipitate with the monohydrochloride salt that are extremely difficult to eliminate during the subsequent formation of the histamine dihydrochloride salt. The relationship between the method of salt formation and the generation of contaminants was not appreciated in the art.

Various co-solvents may be used during the addition of HCl in isopropanol to effect precipitation of the monohydrochloride salt form of the molecule (salt precipitation). Co-solvents useable in the invention disclosed herein include: methylene chloride, cyclohexanol, toluene and tert-butyl methyl ether (TBME).

The ultimate purity of the final product is of particular concern. Additional method steps to purify the final product are also contemplated. For example, recrystallization is a process of repeated crystallization in order to purify a substance. A number of solvents are contemplated for use in this purification process. These solvents include: methyl chloride, 2-propanol, methanol, ethanol (ETOH), methanol/acetone, water, methanol/ethyl acetate, water/acetone, methanol/ethanol, water/methanol, methanol/hexane, water/methanol/acetone, methanol/methylene chloride, 2-propanol/ethanol, methanol/2-propanol, acetone/2-propanol, acetone/ethanol. From a toxicological viewpoint, a non-toxic solvent such as ETOH is preferred.

The presence of color in the various solutions obtained during the synthesis pathway was observed. Activated carbon may be added to remove some of the color before or as a step of the recrystallization process.

The invention disclosed herein further contemplates the use of derivitizing chemical reactions to assist in the purification of histamine dihydrochloride. Accordingly, it is contemplated that chemical derivatives of various impurities would be made during the histamine dihydrochloride process of the invention disclosed herein to facilitate the removal of those impurities. The creation of one such derivative involves the addition of a tert-butoxycarbonyl group to a molecule of interest. Other modifying groups such as benzyloxycarbonyl groups (CBZ) are also contemplated.

The following examples discuss methods addressing the decarboxylation of histidine as well as the isolation of the histamine product. Also discussed are methods of purification of the crude histamine dihydrochloride product using multiple recrystallization steps. Charcoal mediated decoloration is also discussed.

The efficiency of various method steps as well as the purity of the final product may be analyzed using the methods desired below. One or more monitoring steps may be used to assay the efficiency of the decarboxylation step. Alternatively, various assay methods well known in the art may be used to analyze the purity of the final product. An example of such a monitoring step is the performance of thin layer chromatography (TLC), a procedure well known in the art, on various reaction products. For example, reactions could be monitored using TLC (mobile phase: $CH_3CN:H_2O:NH_4OH$; 7.5:2.0:0.5; and ninhydrin spray). This monitoring step may be performed anytime after the decarboxylation step.

Particular embodiments of the invention are discussed in detail below. The following examples are for illustrative purposes only and should not be interpreted as limitations of the claimed invention. There are a variety of alternative techniques and procedures available to those of skill in the art which would similarly permit one to successfully perform the intended invention.

EXAMPLES

Preparation of Histamine Dihydrochloride

The following Examples discuss the synthesis of histamine dihydrochloride from the precursor compound L-histidine. Existing histamine synthesis protocols, while capable of yielding histamine dihydrochloride, suffer from the limitation of producing an impure final product. The Examples below discuss various improvements in histamine dihydrochloride synthesis and teach the preparation of a pharmaceutically acceptable grade of histamine dihydrochloride.

Example 1

Preparation of 500 Grams of Crude Histamine Dihydrochloride

A method for the synthesis of a 500 gram sample of histamine dihydrochloride is described below.

A twelve liter (12-L), 4 necked, round-bottom flask equipped with a thermometer, mechanical stirrer, condenser and nitrogen bubbler was charged with 7.5 L of cyclohexanol (the solvent), 750 grams of L-histidine (the substrate) and 113 ml of acetophenone (the catalyst). The suspension was agitated in a nitrogen atmosphere that was maintained throughout the reaction.

The suspension was heated to reflux and maintained at that temperature (150–165° C.) for a minimum of 40 hours. A small sample was withdrawn for an in-process assay to determine the extent of histidine decarboxylation. The suspension was cooled to below 80° C. and 1875 ml of toluene was charged. This mixture was further cooled to room temperature. The mixture was filtered through a Buchner funnel into a fresh 12-L, 4 necked round-bottom flask.

The fresh flask containing the filtrate was equipped with a thermometer, mechanical stirrer, hydrogen chloride trap and vacuum trap, and prepared for gaseous hydrogen chloride addition. With agitation, the solution was cooled to below 10° C. Maintaining the batch temperature below 20° C., a minimum of 441 grams (2.5 equivalents) of gaseous hydrogen chloride was charged. Upon completion of the hydrogen chloride addition, the resulting thick yellowish suspension was agitated at room temperature for one hour.

The suspension was again filtered through a Buchner funnel. The filter cake was rinsed with a mixture of 375 ml of cyclohexanol and 375 ml of toluene, followed by two 750 ml washes of toluene and two 750 ml rinses of hexanes. The cake was dried on the filter with suction for a minimum of 30 minutes. The filter cake contained a substantial amount of cyclohexanol which was removed through trituration.

The wet filter cake was charged to a 12-L 4-necked round-bottom flask equipped with a mechanical stirrer and nitrogen bubbler. Ethanol (ETOH) in a volume of 7.5 L was also charged. The suspension was agitated at room temperature for 4 hours. The suspension was filtered through a Buchner funnel and the filter cake rinsed with 400 ml of hexanes. The filter cake was dried in a vacuum oven at 60–65° C. overnight. The product of this method produced 504 of crude histamine dihydrochloride grams (a 56.6% yield) at 94.4% a/a purity determined using high performance liquid chromatography (HPLC). The product was recrystalized to improve the purity of the final product.

A 12-L, 4-necked, round-bottomed flask equipped with a thermometer, mechanical stirrer, condenser, addition funnel and nitrogen bubbler was charged with the 503 grams of crude histamine dihydrochloride product synthesized above. Additionally, 4.5 L of ETOH and 200 ml of water were added to the reaction flask to dissolve the filter cake. The suspension was agitated under a nitrogen atmosphere.

The suspension was heated to reflux. Maintaining the suspension under reflux, water was charged drop-wise to the suspension until most of the solids were dissolved. The solution was cooled to below 75° C. The solution was charged with a mixture of 50 grams of NUCHAR SA (Westvaco, New York, N.Y.) and 50 grams of CELITE (J. T. Baker, Hayward, Calif.). This suspension was heated then heated to reflux and maintained at that temperature for 0.5 hours. The suspension was cooled to 65–75° C. and then filtered through a CELITE bed into a clean, dry 12-L, 4-necked, round-bottom flask. The filter cake was rinsed with a mixture of 450 ml of ETOH and 50 ml of water.

The filtered solution was slowly cooled to room temperature with stirring overnight. The solution was further cooled to 0–5° C. for 2 hours. At 0–5° C., the suspension was filtered through a Buchner funnel. The filter cake was washed three times with 200 ml of ETOH chilled to 0–5° C. The filter cake was dried in a vacuum oven at 60–65° C.

After recrystallization, the final product was 299 grams, (a 59.4% yield), at 99.1% a/a HPLC purity. The HPLC protocol is discussed in Example 7 below. Additional rounds of recrystallization were performed to increase the purity of the final product. However, two unknown impurities, (RRt 1.3, 1.5) were still present above the 0.1% threshold level after recrystallization.

Typically, the first impurity (RRt 1.3) was at 0.2–0.4% a/a and the second impurity (RRt 1.5) at 0.5–0.6%. A second recrystallization of the sample discussed above reduced the impurity levels to 0.1–0.2% and 0.4–0.5%, respectively. The impurities appeared to grow when the samples were reanalyzed after a number of days, indicating stability concerns for the final product. Instability of the product might explain why the wet filter cake discussed above showed 99.9% a/a HPLC purity but only 99.1% was obtained after the batch was dried. Subsequent treatments with dichloromethane or charcoal treatments were unable to remove the impurities.

Example 2

Catalysts for the Decarboxylation of L-Histidine

In view of the results discussed above, a number of modifications to the synthesis method were undertaken. These modifications sought to reduce the levels of the unknown impurities to an acceptable level. One variable examined concerned the nature of the catalyst used in the decarboxylation reaction. A variety of other catalysts were examined, including acetophenone, to determine what role, if any, they play in the formation of the chromatographic impurities. Table 1 shows the catalysts used in this study. The catalysts were used at 0.3 equivalents.

TABLE 1

Survey of Decarboxylation Catalysts

| Catalyst | Reaction Time (h) | HPLC Purity (% a/a) | |
|---|---|---|---|
| | | Impurity #1 | Impurity #2 |
| Acetophenone (control) | 21 | 4.5 | 4.0 |
| 4'-Bromoacetophenone | 21 | 7.0 | 3.4 |
| Benzophenone | 21 | 14.5 | 2.9 |
| p-Nitroacetophenone | 17 | Decomposition | Decomposition |
| p-Methylacetophenone | 16 | 1.65 | 0.71 |
| p-Methyloxyacetophenone | 16 | 1.9 | 2.9 |
| p-Methylacetophenone/1-methyl-4-piperidone | 7.5 | 3.0 | 2.4 |
| p-Methylacetophenone/AcOH | 7.5 | 9.6 | 3.5 |

The results in Table 1 indicate that p-methylacetophenone was superior to acetophenone at diminishing the level of impurities found in the final product. In contrast, using p-methylacetophenone in conjunction with a base (1-methyl-4-piperidone) showed no improvement in the level of impurity generation, while introducing an acid (acetic acid) considerably elevated the impurities found in the final product. Further, p-methoxyacetophenone offered an advantage over acetophenone with respect to contaminant generation, but did not produce a significant enhancement versus p-methylacetophenone upon isolating the monohydrochloride salt. The data suggest that catalysts with an electron-deficient ketone exhibit an increase in the generation of impurities found in the final product, whereas electron-enriched ketones showed a decrease in impurity generation. Based on these results, acetophenone was replaced with p-methylacetophenone as the catalyst used in the decarboxylation reaction of the invention disclosed herein.

Example 3

Methods of Producing Histamine Salt Forms

Another parameter explored, which concerned the generation of acceptably pure histamine dihydrochloride, involved the molar equivalency of acid added during the precipitation of the crude salt. It is one of the surprising discoveries of the invention disclosed herein that a reduction in the amount of contaminants present in the final product is related to the amount of acid used to create the salt form of the molecule. In prior art procedures a quantity of 2.5 molar equivalents of hydrogen chloride (HCl) gas was introduced into a solution containing the decarboxylated histidine (histamine free base) to generate a crude dihydrochloride salt. The present Example examines the effect of adding a variety of molar equivalents of hydrochloric acid to the histamine free base solution by introducing the acid dissolved in isopropanol (ISA).

A variety of HCl concentrations were dissolved in ISA and tested for their effects on the production of impurities. The synthesis protocol was followed as described above except that 0.3 equivalents of p-methylacetophenone with toluene as the co-solvent for the addition of the HCl were used. The HPLC protocol of Example 7 below was used to determine the presence of impurities. The results of this range of acid concentrations are listed in Table 2 below.

TABLE 2

Equivalents of HCl and Their Effect of Impurity Generation

| Molar Equivalents of HCl/IPA | HPLC Purity (% a/a) | | Condensation Product |
|---|---|---|---|
| | Impurity #1 | Impurity #2 | |
| 2 (control) | 2.5 | 2.35 | 22.0 |
| 1.4 | 2.0 | 2.1 | 6.5 |
| 0.9 | 0.55 | 1.15 | 2.1 |
| 0.5 | 0.06 | 0.83 | 0.45 |

The results shown in Table 2 illustrate how the amount of acid charged to the solution containing the histamine free base dramatically altered the level of the two impurities present in the product. The observed decrease was likely attributable to the impurities possessing less of a basic character than that of the histamine free base. As a consequence, the histamine free base likely undergoes protonation first followed by the impurities.

The use of 0.5 molar equivalents of HCl provided the most favorable results with regards to limiting the levels of impurities found in the product. Under these conditions, the crude product isolated was the monohydrochloride salt as determined by titration for chloride content. Accordingly, to synthesize a dihydrochloride form of histamine of an acceptably high purity, an intermediate purification step involving the intentional generation of monohydrochloride salt was adopted. Using this method, however, it would be necessary to add an additional equivalent of HCl in a later synthesis step so as to produce the dihydrochloride form of the molecule.

Additional experiments were performed to examine the effect of small changes in acid concentration on product purity and yield. The results of these experiments are shown in Table 3. These results were taken from products formed from a 100 ml reaction mixture with 0.3 equivalents of p-methylacetophenone and $CH_2Cl_2$ as the co-solvent. The selection of $CH_2Cl_2$ is discussed in detail in Example 4.

TABLE 3

Small Variations of Acid Equivalents and Their Effect on Product Formation

| | CRUDE SALT | | | FINAL PRODUCT | |
|---|---|---|---|---|---|
| | | HPLC Purity (% a/a) | | | HPLC Purity (% a/a) |
| HCl (eq.) | Yield % | Impurity #1 | Impurity #2 | Yield % | Impurity #1 | Impurity #2 |
| 0.57 | 43.3 | 0.05 | 0.14 | 57.7 | 0.03 | 0.07 |
| 0.67 | 50.6 | 0.06 | 0.17 | 61 | 0.05 | 0.10 |
| 0.76 | 53.5 | 0.09 | 0.20 | 59 | 0.05 | 0.1 |

The equivalency window was narrowed to determine the effect that relatively small variation in the amount of acid had on the impurity profile in the crude salt. The data shown in Table 3 support the previous observation that a decrease in the quantity of acid charged results in a decrease in the amount of impurities found in the final product, as well as a decrease in the yield. In future experiments 0.6 molar equivalents of HCl versus the starting material was used. For larger amounts of product using larger amounts of starting material, the amount of acid required is 0.85 molar equivalents of HCl per mole of free base, as determined by assay. This amount of HCl calculated represents approximately 0.6 molar equivalents versus the starting material of L-histidine.

Example 4

Co-solvents for Use During Salt Formation

The next variable examined to improve the synthesis of histamine dihydrochloride concerned co-solvent used during the acid addition step of the procedure. Previously, toluene was used as the co-solvent. To explore the possible effect of the co-solvent on the purity of the final product, a variety of co-solvents were used in the precipitation step. As above, the purity of the resulting samples was assayed using the HPLC method described in Example 7. The results are shown in Table 4.

TABLE 4

The Effect of Methylene Chloride and Other Co-solvents on Final Product Purity

| Co-solvent | % Yield | HPLC Purity (% a/a) | |
|---|---|---|---|
| | | Impurity #1 | Impurity #2 |
| Toluene (control) | 49.5 | 0.13 | 0.31 |
| $CH_2Cl_2$ | 45.9 | 0.10 | 0.15 |
| TBME | 51.9 | 0.33 | 0.51 |
| None | 43.5 | 0.12 | 0.18 |

The reaction conditions for the results produced in Table 4 were p-methylacetophenone present in 0.3 equivalents, 0.6 equivalents of HCl/IPA and 5 parts of co-solvent for precipitation. The results in Table 4 show that methylene chloride provides superior results with respect to impurity formation as compared to other co-solvents.

Example 5

Preparation of Crude Histamine Monohydrochloride

The procedure described below teaches the preparation of histamine monohydrochloride. A two liter (2-L), 3-necked, round-bottomed flask (the reactor) was equipped with a thermometer, mechanical stirrer, condenser and nitrogen purge system was charged with 1 L of cyclohexanol, 100 gm of L-histidine and 25.9 ml of p-methylacetophenone. Cyclohexanol has a melting point of 22-22° C. and may require heating to generate a liquid that can be transferred to the reactor. The suspension had a white coloration, with a temperature of between 20–25° C. and a volume of 1050 ml. The suspension was agitated in the presence of a nitrogen atmosphere that was maintained throughout the reaction.

The suspension was heated to reflux (160–165° C.) and maintained under reflux for 30 hours. A small sample was withdrawn to determine what percentage of the starting material had been decarboxylated. The suspension should contain $\leq 1\%$ a/a L-histidine. In the event of an incomplete reaction, continue heating the suspension at reflux for an additional 3–5 hours and then resample. The formation of a clear, homogenous solution indicates the consumption of the starting material and the completion of the decarboxylation reaction.

Once the reaction was complete, the suspension was cooled to about 20–25° C. Then the reactor was charged with 300 ml of methylene chloride. This mixture was further cooled to room temperature. The mixture was filtered through a Buchner funnel into another 2-L 3-necked round-bottomed flask. The first reactor was then washed twice with 100 ml methylene chloride that was then used to rinse the filter. This filtration step removed any residual L-histidine.

The second reactor containing the filtrate was equipped with a thermometer, mechanical stirrer, addition funnel and nitrogen purge system. After the washing step and the reestablishment of the nitrogen atmosphere in the reactor, the filtrate was heated to 30–35° C. An aliquot of the solution was withdrawn and assayed for the content of histamine free base. The results from the assay were used to calculate the amount of acid required to generate the monohydrochloride salt. The amount of acid required was 0.85 molar equivalents of HCl per mole of histamine free base.

With vigorous agitation, 50.5 ml of a 7.65M HCl isopropanol (HCl/ISA) solution was added dropwise at a rate where the temperature of the solution did not exceed 40° C. Given the exothermic nature of this method step, addition of the HCl/ISA solution occurred over the time of an hour. The resulting light beige suspension was allowed to cool to 20–25° C. over 1 hour and agitated for a minimum of 2 hours. The 7.65 M HCl in isopropanol solution was prepared by bubbling 27.9 g of HCl gas into 100 ml of isopropanol chilled to 5–10° C.

The cooled suspension was filtered through a Buchner funnel under a stream of nitrogen and the filter cake rinsed three times with 100 ml of a 1:1 methylene chloride/cyclohexanol solution. The filter cake was then washed three times with 100 ml of methylene chloride. Since the monohydrochloride salt was readily soluble in water, the humidity of the laboratory may have an effect on the yield of the product. Therefore, exposure of the filter cake to moisture during the filtration step was minimized by performing the operation under a stream of nitrogen.

The wet filter cake was then charged to a 1 L, 3-necked round bottom flask equipped with a thermometer, mechanical stirrer and nitrogen purge system for methylene trituration. The solid was suspended in 500 ml of methylene chloride and agitated for 1 hour under nitrogen. The methylene trituration assisted in the removal of residual cyclohexanol and enabled the product to be dried more effectively, as was seen in the subsequent steps described below.

The suspension, under a stream of nitrogen, was filtered and the solid material was washed twice with 75 ml of methylene chloride. The filter cake was dried in a vacuum oven at 55–60° C. for 16 hours.

Table 5 below shows the results of the method described in this Example. This method was practiced three times and the product yields from each were compared.

TABLE 5

Crude Yields of Histamine Monohydrochloride

|  | Experiment 1 | Experiment 2‡ | Experiment 3‡ |
|---|---|---|---|
| Weight of Dry Solid† | 50.28 | 52.29 | 50.28 |
| % Crude Yield | 52.9 | 55.0 | 52.9 |

†Weight of solids and corresponding percentage yields were corrected for solvent content.
‡In Experiments 2 and 3, the filter cake was dried for 8 rather than 16 hours.

Example 6

Preparation of Histamine Dihydrochloride by Decarboxylation of L-Histidine

Example 6 shows a procedure for the synthesis of histamine dihydrochloride from the monohydrochloride precursor product produced with the method of Example 5.

A one liter (1 L) three-necked, round bottom flask (the reactor) equipped with a mechanical stir bar, an addition funnel, a condenser, a nitrogen purge system, and thermometer was placed in a heating mantle. The reactor was charged with 40 grams of histamine monohydrochloride, 32 ml $H_2O$ (distilled), and 280 ml of a 1×ETOH solution consisting of 99.5% ETOH and 0.5% toluene. A nitrogen atmosphere was maintained throughout the reaction as the histamine monohydrochloride salt was very hygroscopic.

The next step of the method entailed the addition of a HCl/ISA solution to convert the histamine monohydrochloride salt to the dihydrochloride form. To the reactor was added 41.5 ml of 6.85M HCl/ISA solution (1.05 equivalents). As discussed above, the addition of the acid solution was exothermic, therefore, the acid was added over a 15 minute time frame. During the initial stages of the acid addition, a clear solution was generated, however this quickly returned to a thick off-white suspension after approximately 75% of the acid was introduced.

After addition of the acid was complete, the resulting thick, off-white suspension was heated to reflux (78–80° C.) in an oil bath. The solid matter in the suspension gradually dissolved to form an amber solution. Once the solid matter was completely dissolved, the reactor was removed from the oil bath. The reactor was then charged with NUCHAR SA charcoal (2 grams) and CELITE (2 grams). This suspension was heated to reflux for 25 minutes. Maintenance of temperature was important as the product would precipitate at about 60° C.

The hot, black suspension was filtered through a bed of CELITE into a fresh 1 L, 3-necked, round bottom flask equipped with a mechanical stirrer and thermometer. The CELITE bed served as a barrier to prevent the flow of the charcoal through the filtering unit. The fresh reactor had been pre-heated in an oil bath and the charging of the reactor also occurred in this oil bath.

The first reactor containing the reaction mixture was rinsed twice with 40 ml of ETOH 1× solution at a temperature of 60–65° C. This solution was filtered and added to the filtrate produced above. The addition of the rinse volume produced some precipitate in the filtrate. The total volume of solution was then agitated by stirring at 60–65° C. for 30 minutes.

The suspension (histamine dihydrochloride) was then slowly cooled to 25° C. over 1 hour, and agitated at 20–25° C. for 2 hours and then cooled to 0–5° C. for 2 hours hours. The suspension was then filtered under a stream of nitrogen and the filter cake washed three times with 40 ml of cold ETOH 1×. The filter cake was then weighed and dried in a vacuum oven at 55–60° C. for 16 hours. The results of three different experiments converting histamine monohydrochloride to the dihydrochloride salt form are shown in Table 6.

TABLE 6

Yields of Histamine Dihydrochloride

|  | Experiment 4 | Experiment 5 | Experiment 6 |
|---|---|---|---|
| Weight of Wet Cake (grams) | 48.8 | 45.6 | 46.4 |
| Weight of Dry Solid (grams) | 34.9 | 33.3 | 33.6 |
| % Yield⁻ | 70 | 66.7 | 67.4 |

⁻The percent yield FIG. was based on the histamine monohydrochloride corrected for solvent content.

Example 7

An HPLC Method to Assay, Identify and Determine Purity of Histamine Dihydrochloride This example discusses the use of HPLC to quantitate and identify histamine dihydrochloride and to quantitate related substances and degradants in the final product. The method employed a complete HPLC system with gradient and UV detection capabilities. For chromatographic purity determinations, a system containing a computerized data acquisition system was utilized. Other equipment used included: a Waters Symmetry C-18, 5 μm, 4.6×350 mm column; an analytical balance with 0.01 mg or 0.01 g resolution; volumetric glassware; and a column heater. Reagents and standards used included: a USP histamine dihydrochloride reference standard or equivalent; methanol, HPLC grade; acetonitrile, HPLC grade; 1-heptane sulfonic acid, sodium salt, Fisher Scientific (Pittsburgh, Pa.) HPLC grade or equivalent; sodium phosphate, monobasic, monohydrate, ACS reagent grade; D-, L-histidine monohydrochloride, monohydrate, (Sigma, St. Louis, Mo.); 1 N sodium hydroxide solution; 1 N hydrochloric acid solution; purified water; and benzyl alcohol, ACS reagent grade or equivalent.

Two mobile phase buffers were prepared. Mobile Phase A (MPA) contained 0.02 M sodium phosphate monobasic and 0.005 M heptanesulfonic acid, pH adjusted to 3.0. Mobile phase B (MPB) contained acetonitrile (ACN)/methanol (MeOH): 20/15 (v/v).

Standards and samples were prepared for the assay and chromatographic purity determinations. The assay standards involved the preparation of histamine dihydrochloride standard solutions at three concentrations, 0.88 mg/ml, 0.80 mg/ml, and 0.72 mg/ml. DL-histidine monohydrochloride, monohydrate standards were prepared at 0.008 mg/ml. Similarly, assay samples were prepared in duplicate to contain 0.8 mg/ml of synthetically produced histamine dihydrochloride while limit of quantitation (LOQ) solution was prepared at 0.0006 mg/ml of histamine dihydrochloride. The sensitivity of the method for Histamine has been determined to be 0.07% for the limit of quantitation and 0.03% for the limit of detection. Photodiode array peak purity studies have demonstrated the specificity for histamine.

Following preparation of the various standards and samples, the HPLC system was equilibrated. Once equilibrated, the flow rate from the waste line was checked at the initial condition setting (i.e., 10% MPB at 1.5 ml/minute). The flow rate was 1.5 ml/minute±0.15 ml/minute. A water blank injection was made after the system equilibrated to condition the column prior to the start of the assay.

Once these preparations were complete, the resolution solution of 0.7 mg/ml±0.1 mg/ml histamine dihydrochloride was injected. The resolution "R" between a 1 mg/ml benzyl alcohol solution peak and histamine peaks was calculated. Further, this process was repeated five (5) times and a standard deviation was calculated.

For the assay, a standard curve was generated. The standard check was performed every four to six sample injections and fell within the following parameters: the tailing factor was not>2.0; the resolution was>1.5, the relative standard deviation of the histamine peak responses was not>2.0%; and the correlation coefficient of the standard curve was not less than 0.995.

To calibrate the chromatographic purity, a single injection of the resolution solution was made. The resolution "R" between benzyl alcohol and the histamine peaks was calculated and so was the tailing factor of the histamine peak. Since the resolution and tailing factors met the specifications, three consecutive injections of the LOQ sample were performed.

The relative standard deviation for the three histamine peak responses were calculated. In general, the tailing factor was not>2.0, the resolution was greater than 1.5, and the relative standard deviation of the histamine peak responses was not greater than 10%.

Since the above parameters were met, the final histamine dihydrochloride samples were tested. The operating parameters for the HPLC are listed in Table 7. The gradient parameters are listed in Table 8.

TABLE 7

| Operating Parameters | |
|---|---|
| Flow Rate: | 1.5 ml/minute |
| Injection Volume: | 20 μl |
| Detection: | 212 nm |
| Column: | Waters Symmetry C-18, 5 μm, 4.6 mm × 250 mm |
| Column Temperature: | 50° C. |
| Assay Concentration: | 0.8 mg/ml histamine dihydrochloride |
| Run Time: | about 30 minutes |
| Mobile Phase A: | buffer solution |
| Mobile Phase B: | ACN/MeOH 20/15 (v/v) |

TABLE 8

| Gradient Parameters | | |
|---|---|---|
| Time (min) | % Mobile Phase B | Flow Rate (ml/min) |
| 0 | 10 | 1.5 |
| 20 | 30 | 1.5 |
| 21 | 10 | 1.5 |
| 30 | 10 | 1.5 |
| Retention times: | histidine = approximately 3 minutes | |
| | histamine = approximately 12 minutes | |

Use of this analytical system provided the method required to determine histamine dihydrochloride sample produced in the aforementioned examples.

Example 8

HPLC Analysis of Histamine Dihydrochloride Product

The histamine dihydrochloride products from Example 6 were subjected to the HPLC analysis described in Example 7 to determine the purity of the samples and to establish whether the final products met the criteria of purity set for the method of the invention disclosed herein. For use as a pharmaceutical agent, the histamine dihydrochloride must possess minimal chromatographic impurities. Individual impurities found at levels above 0.1% a/a generally require toxicological qualification. Three lots of histamine dihydrochloride were generated using the methods of Examples 5 and 6. Their purity is described in Table 9.

TABLE 9

| HPLC Analysis Results | | |
|---|---|---|
| Experiment | Description of Impurities | Specification/Found |
| Experiment 1 | L-histidine HCl monohydrate | <0.8% w/w; Not detected |
| | Individual chromatographic impurities | <0.1% w/w |
| | Impurity #1 | <0.05% w/w |
| | Impurity #2 | 0.13% w/w |
| | Total chromatographic impurities | <2.0% w/w; 0.2% w/w |

TABLE 9-continued

HPLC Analysis Results

| Experiment | Description of Impurities | Specification/ Found |
|---|---|---|
| Experiment 2 | L-histidine HCl monohydrate | <0.8% w/w; Not detected |
| | Individual chromatographic impurities | <0.1% w/w |
| | Impurity #1 | <0.05% w/w |
| | Impurity #2 | 0.10% w/w |
| | Total chromatographic impurities | <2.0% w/w; 0.2% w/w |
| Experiment 3 | L-histidine HCl monohydrate | <0.8% w/w; Not detected |
| | Individual chromatographic impurities | <0.1% w/w |
| | Impurity #1 | <0.05% w/w |
| | Impurity #2 | 0.06% w/w |
| | Total chromatographic impurities | <2.0% w/w; 0.1% w/w |

The results described in Table 9 show that the final histamine dihydrochloride product falls within acceptable standards set for the invention disclosed herein. First the level of Impurity #1 was found to be below the limit of quantitation for the assay. Second, Impurity #2 was found at levels slightly above the 0.1% threshold and will therefore be qualified through toxicological testing. The specification level for impurity has been established as <0.2% w/w. These results show that the synthesis method of the invention disclosed herein provides a means to synthesize a pharmaceutically acceptable form of histamine dihydrochloride.

Conclusion

The invention disclosed herein describes a novel, non-enzymatic method for producing pharmaceutical grade histamine dihydrochloride. One significant advantage of the method described herein is that it yields histamine dihydrochloride at a purity level higher than is otherwise presently available.

Finally, the forgoing examples are not intended to limit the scope of the present invention, which is set forth in the following claims. In particular, various equivalents and substitutions will be recognized by those of ordinary skill in the art in view of the foregoing disclosure, and these are contemplated to be within the scope of the disclosed invention.

What is claimed is:

1. A method for the synthesis of histamine dihydrochloride comprising:

forming a histamine monohydrochloride solution by catalytic decarboxylation of a L-histidine solution wherein the catalyst is selected from the group consisting of benzoyl peroxide, 2,2'-azobisisobutyronitrile (AIBN), 2-cyclohexen-1-one, acetophenone, 4'-bromoacetophenone, benzophenone, p-nitroacetophenone, p-methylacetophenone, p-methoxyacetophenone, p-methylacetophenone/1-methyl-4-piperidone, and p-methylacetophenone/AcOH, and addition of hydrogen chloride thereto; and forming a histamine dihydrochloride solution from the histamine monohydrochloride solution by addition of hydrogen chloride, wherein the resulting histamine dihydrochloride solution comprises less than 2% total impurities as measured by HPLC analysis.

2. The method of claim 1, wherein the histamine monohydrochloride solution is formed by triturating the decarboxylated L-histidine solution.

3. The method of claim 2, wherein the histamine monohydrochloride solution is triturated with a methylene chloride solution.

4. The method of claim 1, wherein the histamine monohydrochloride solution is formed by addition of an effective amount of hydrochloric acid in an isopropanol solution.

5. The method of claim 4, wherein the effective amount of hydrochloric acid is about 0.1 to 0.9 molar equivalents of hydrochloric acid to histamine free base.

6. The method of claim 4, wherein the effective amount of hydrochloric acid is is about 0.6 molar equivalents of hydrochloric acid to histamine free base.

7. The method of claim 4, wherein the histamine dihydrochloride contains equal to or less than each of the followings: 0.8% L-histidine HCl monohydrate, 0.1% individual chromatographic impurities, and 2% total impurities.

8. Histamine dihydrochloride prepared by forming a histamine monohydrochloride solution by catalytic decarboxylation of a L-histidine solution wherein the catalyst is selected from the group consisting of benzoyl peroxide, 2,2'-azobisisobutyronitrile (AIBN), 2-cyclohexen-1-one, acetophenone, 4'-bromoacetophenone, benzophenone, p-nitroacetophenone, p-methylacetophenone, p-methoxyacetophenone, p-methylacetophenone/1-methyl-4-piperidone, and p-methylacetophenone/AcOH, and addition of hydrogen chloride thereto; and forming a histamine dihydrochloride solution from the histamine monohydrochloride solution by addition of hydrogen chloride, wherein the resulting histamine dihydrochloride comprises less than 2% total impurities as measured by HPLC analysis.

* * * * *

UNITED STATES PATENT AND TRADEMARK OFFICE
CERTIFICATE OF CORRECTION

PATENT NO. : 6,528,654 B2
DATED : March 4, 2003
INVENTOR(S) : Yeh et al.

It is certified that error appears in the above-identified patent and that said Letters Patent is hereby corrected as shown below:

Column 16,
Line 15, cancel "monohydrochioride" and replace it with -- monohydrochloride --.
Line 28, cancel "is is" and replace it with -- is --.
Line 32, cancel "followings:" and replace it with -- following: --.

Signed and Sealed this

Eighteenth Day of May, 2004

JON W. DUDAS
*Acting Director of the United States Patent and Trademark Office*